US00PP35050P2

(12) United States Plant Patent
Ranney et al.

(10) Patent No.: US PP35,050 P2
(45) Date of Patent: Mar. 21, 2023

(54) ***BERBERIS* PLANT 'NCBT3'**

(50) Latin Name: *Berberis thunbergii*
Varietal Denomination: NCBT3

(71) Applicant: North Carolina State University, Raleigh, NC (US)

(72) Inventors: Thomas Green Ranney, Arden, NC (US); Darren H. Touchell, Arden, NC (US); Andra Windorf Nus, Arden, NC (US); Irene Palmer, Arden, NC (US); Nathan Lynch, Arden, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 17/845,433

(22) Filed: Jun. 21, 2022

(51) Int. Cl.
*A01H 5/00* (2018.01)
*A01H 6/00* (2018.01)

(52) U.S. Cl.
USPC ..... Plt./241

(58) Field of Classification Search
USPC ..... Plt./263.1, 308
See application file for complete search history.

*Primary Examiner* — Karen M Redden
(74) *Attorney, Agent, or Firm* — Cassandra Bright

(57) ABSTRACT

A new and distinct cultivar of *Berberis thunberghii* plant named 'NCBT3' is disclosed, characterized by a strongly upright habit and colorful orange-red foliage with gold margins. The new variety is a *Berberis*, typically produced as an ornamental plant.

3 Drawing Sheets

Latin name of the genus and species: The Latin name of the novel plant variety disclosed herein is *Berberis thunbergii*.

Variety denomination: The inventive seedling of *Berberis thunbergii* disclosed herein has been given the varietal denomination 'NCBT3'. Prior to the designation of the varietal denomination, 'NCBT3' was referred to by its experimental code: H2012-077-001.

BACKGROUND OF THE INVENTION

The present invention comprises a new and distinct barberry cultivar hereinafter referred to by the cultivar name 'NCBT3'. This new barberry was developed through a breeding program in, Mills River, N.C. 'NCBT3' was selected in 2012 from a population of seedlings created by the controlled cross of female parent *Berberis thunbergii* 'Aurea Nana' (unpatented) and male/pollen parent *Berberis thunbergii* 'NCBT1' (U.S. Plant Pat. No. 30,330). The crossing resulting in the new variety as conducted during 2011. The first asexual propagation of 'NCBT3' was carried out in July 2014 by rooting stem cuttings at a research nursery in Mills River, N.C. and has been asexually reproduced repeatedly by vegetative cuttings over an 8-year period. 'NCBT3' roots readily from softwood cuttings treated with a basal dip of 3,000-4,000 ppm indole butyric acid (potassium salt) in water. 'NCBT3' has been found to retain its distinctive characteristics through successive asexual propagations.

SUMMARY OF THE INVENTION

The following are the unique combination of characteristics of this new cultivar when grown under standard horticultural practices at a research nursery in Mills River, N.C.

1. Brilliant, red-orange summer foliage with thin gold margins.
2. Compact, upright habit.

PARENT COMPARISONS

Plants of the new cultivar *Berberis thunbergii* 'NCBT3' can be compared to the seed parent, the unpatented *Berberis thunbergii* 'Aurea Nana'. Plants of 'NCBT3' are similar to plants of the seed parent in most horticultural characteristics, however, plants of 'NCBT3' differ in the following:

1. Plants of the new variety have upright, columnar to vase-shaped habits, while plants of the seed parent have dwarf and mounded habits.
2. Foliage of the new variety is red, while foliage of the seed parent is yellow.

Plants of the new cultivar *Berberis thunbergii* 'NCBT3' can be compared to the pollen parent, *Berberis thunbergii* 'NCBT1', U.S. Plant Pat. No. 30,330. Plants of 'NCBT3' are similar to plants of the pollen parent in most horticultural characteristics, however, plants of 'NCBT3' differ in the following:

1. Plants of the new variety have upright, columnar to vase-shaped habits, while plants of the pollen parent have dwarf and mounded habits.
2. Foliage of the new variety is red, while foliage of the pollen parent is greyed-purple.
3. Plants of the new variety are taller than plants of the pollen parent.

COMMERCIAL COMPARISONS

Plants of the new cultivar *Berberis thunbergii* 'NCBT3' can be compared to the commercial variety, *Berberis thunbergii* 'NCBT2', U.S. Plant Pat. No. 33,272. Plants of 'NCBT3' are similar to plants of the commercial variety in most horticultural characteristics, however, plants of 'NCBT3' differ in the following:

1. Plants of the new variety have upright, columnar to vase-shaped habits, while plants of this comparator have low mounded habits.
2. Foliage of the new variety is a darker red, while foliage of this comparator is a brighter red.
3. Plants of the new variety are taller than plants of this comparator.

Plants of the new cultivar *Berberis thunbergii* 'NCBT3' can be compared to the commercial variety, *Berberis thunbergii* 'Maria', U.S. Plant Pat. No. 18,082. Plants of 'NCBT3' are similar to plants of the commercial variety in most horticultural characteristics, however, plants of 'NCBT3' differ in the following:

1. Plants of the new variety have upright, columnar to vase-shaped habits, while plants of this comparator have upright and narrow habits.
2. Foliage of the new variety is red, while foliage of this comparator is yellow.

BRIEF DESCRIPTION OF THE PHOTOGRAPHS

This new barberry is illustrated by the accompanying photographs which show the plant's form and foliage. The colors shown are as true as can be reasonably obtained by conventional photographic procedures. Colors in the photographs may differ slightly from the color values cited in the detailed botanical description, which accurately describe the colors of the new barberry.

DETAILED BOTANICAL DESCRIPTION

Figure 1:
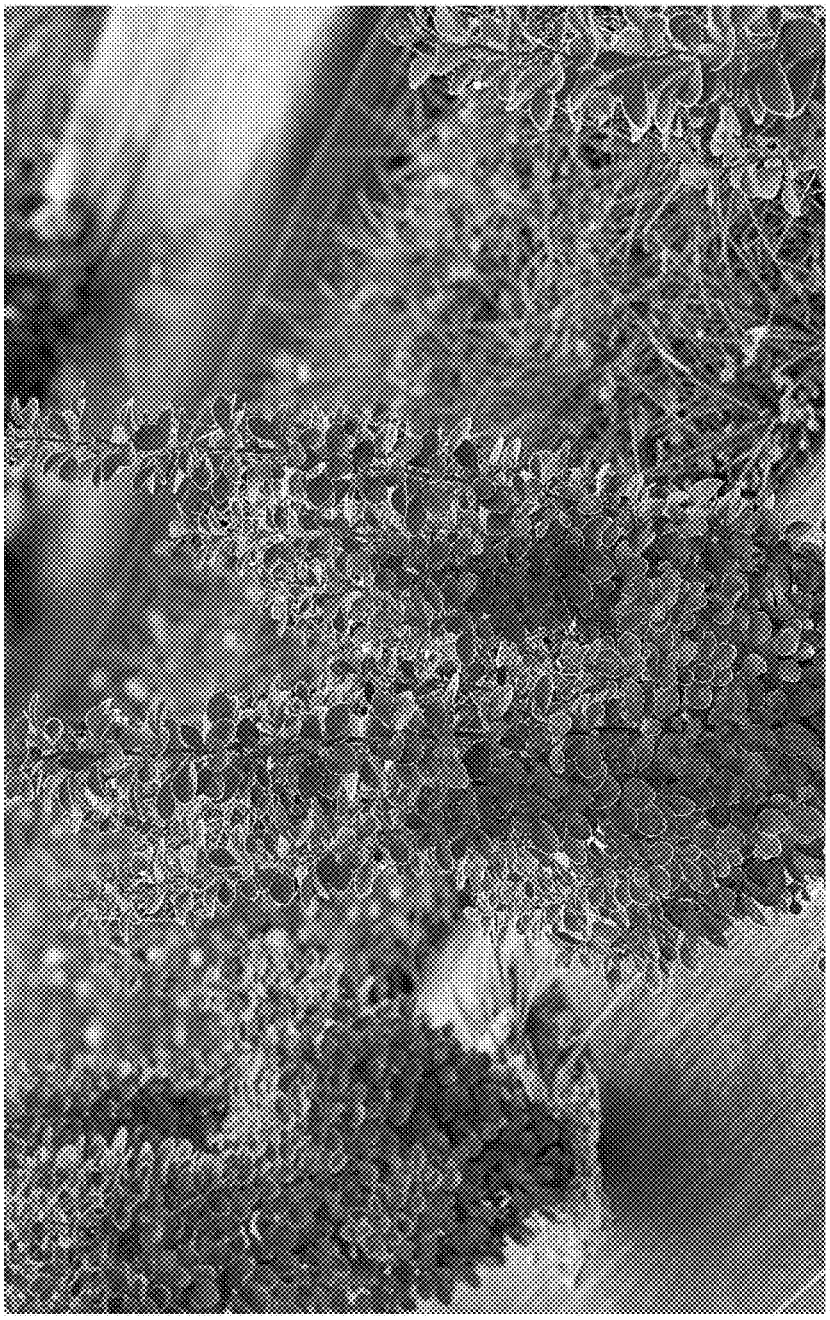
FIG. 1 is a color photograph showing the foliage of 'NCBT3' taken November 2020 in Mills River, N.C.
Figure 2:
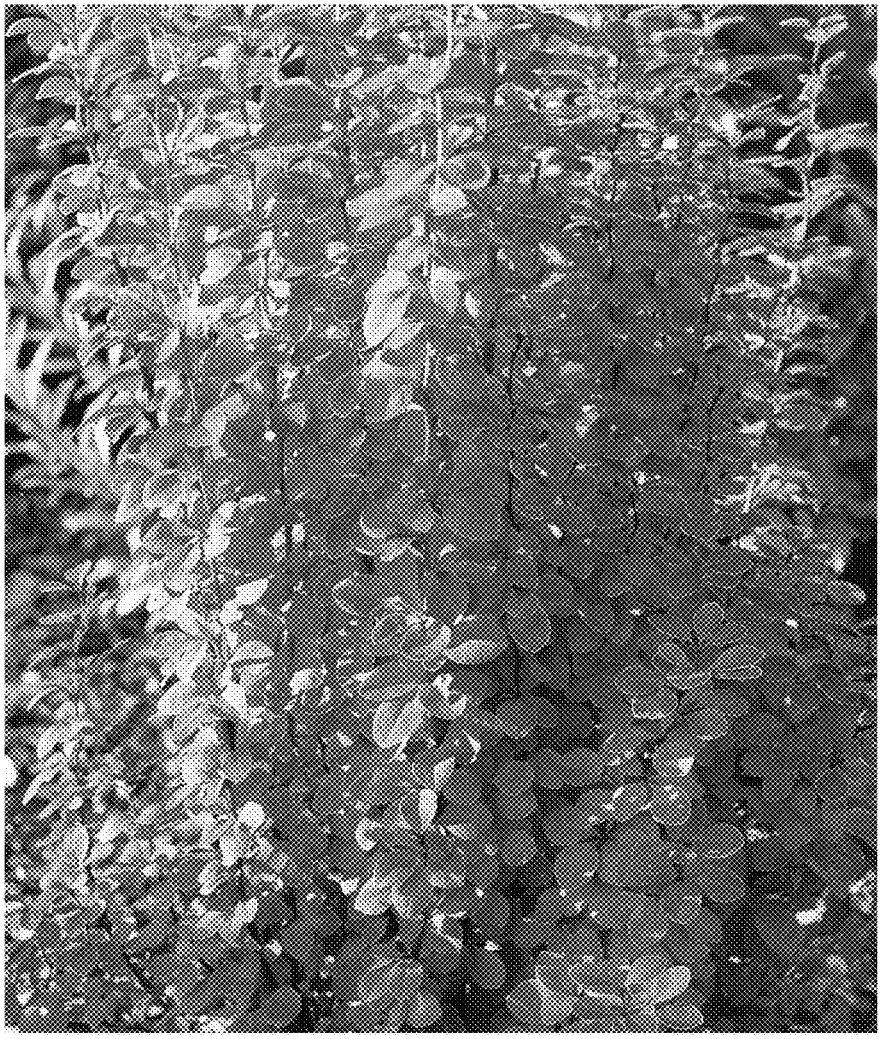
FIG. 2 is a color photograph showing the upright habit of 'NCBT3' taken in April 2021 in Mills River, N.C.
Figure 3:
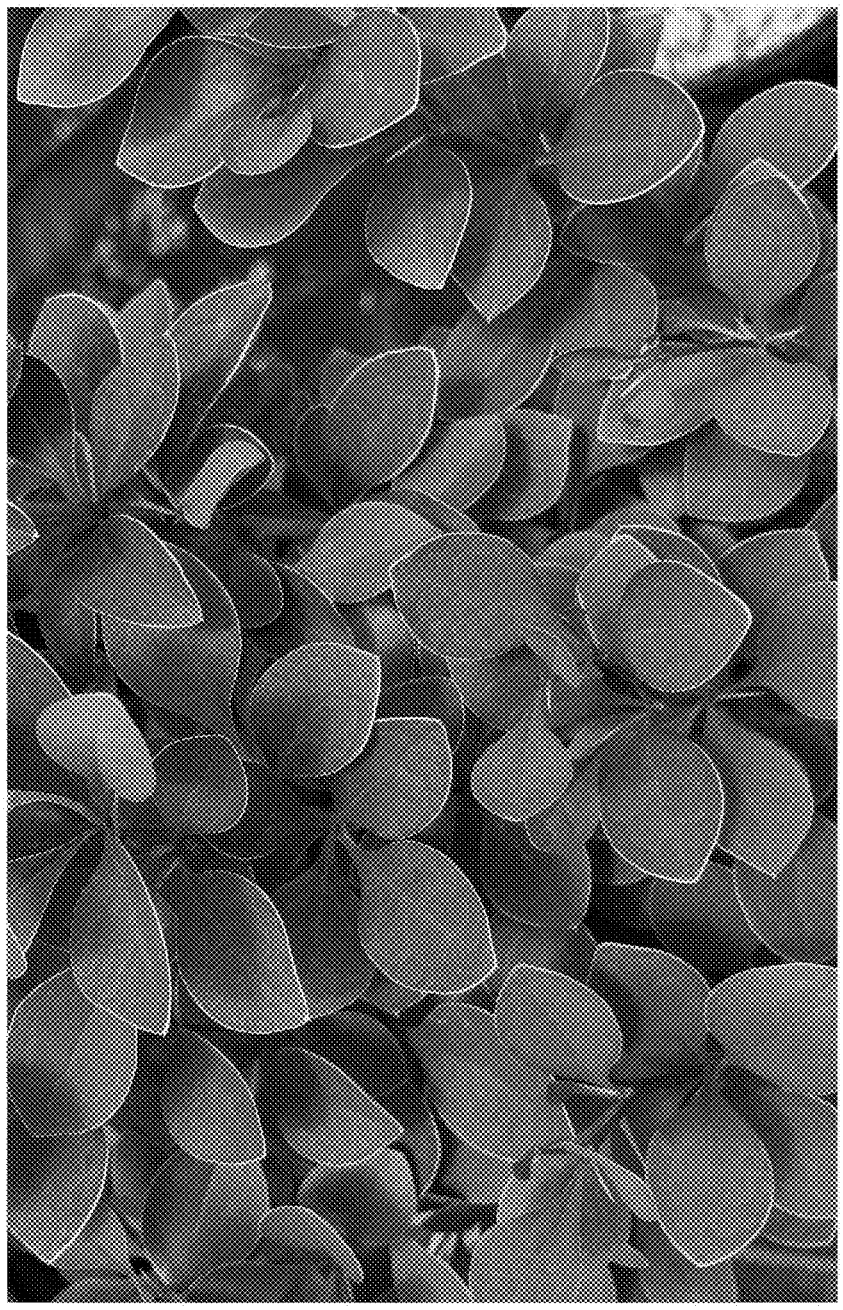
FIG. 3 is a color photograph of the Summer foliage, in full sun of 'NCBT3' taken in July 2021 in Mills River, N.C.

The following is a detailed description of the botanical characteristics of the new and distinct barberry cultivar known by the denomination 'NCBT3'. The detailed description was taken on a seven-year-old field-grown plant in Mills River, N.C. in 2021. All colors cited herein refer to The Royal Horticultural Society Colour Chart (The Royal Horticultural Society (R.H.S.), London, Sixth Edition). Where specific dimensions, sizes, colors, and other characteristics are given, it is to be understood that such characteristics are approximations or averages set forth as accurately as practicable.

Classification:

*Botanical name.*—*Berberis thunbergii* 'NCBT3'.

*Common name.*—Barberry.

Plant description:

*Growth habit.*—Densely branched, upright and columnar to vase-shaped.

*Height.*—125 to 150 cm.

*Width.*—70 to 80 cm.

Shoots and branches:

*Shoots* (*current year's growth*).—Color: Greyed-Orange (RHS 166A). Texture: Glabrous.

*Shoots* (*prior year's growth*).—Color: Brown (RHS N200A). Texture: Glabrous.

*Branches* (*woody branches* 2-4 *years old*).—Branch length: Avg. 80 cm (Range 40 to 130 cm). Branch diameter: Avg. 0.6 cm (0.2 to 1.2 cm). Color: Brown (RHS N200A) with vertical fissures of Brown (RHS N200C). Texture: Glabrous.

*Internode length.*—Avg. 2 cm (1 to 4 cm).

Leaves:

*Type.*—Simple.

*Persistence.*—Deciduous.

*Arrangement.*—Alternate, whorled.

*Shape.*—Obovate.

*Length of lamina.*—Avg. 2.4 cm (1.5 to 3.4 cm).

*Width.*—Avg. 1.5 cm (0.7 to 1.8 cm).

*Apex.*—Obtuse.

*Base.*—Attenuate.

*Margin.*—Entire.

*Color of foliage receiving most sun.*—Upper: Red (RHS 46A) with a narrow margin (about 0.05 cm) of Yellow (RHS 12A). Lower: Greyed-Red (RHS 182C).

*Color of shaded foliage within shrub and on lower branches.*—Upper: Yellow-Green (RHS 144A), with some leaves having a blush of Greyed-Orange (RHS 172D). Lower: Yellow-Green (RHS 144C) with some leaves having a blush of Greyed-Orange (RHS 172D).

*Texture.*—Glabrous.

*Venation.*—Pinnate.

*Vein color.*—Corresponding to the leaf color and varies from Red (RHS 46A), Yellow-Green (RHS 144A) or Greyed-Orange (RHS 172D).

*Leaf attachment.*—Petiolate.

*Petiole.*—Length: Avg. 0.3 cm (0.1 to 0.5 cm). Diameter: About 0.1 cm. Color: Corresponding to the leaf color and varies from Red (RHS 46A), Yellow-Green (RHS 144A) or Greyed-Orange (RHS 172D). Texture: Glabrous.

*Spines.*—Number: 1 per node. Length: Avg. 0.5 cm (0.3 to 0.7 cm). Width: Less than 0.1 cm. Color: Greyed-Red (RHS 179B).

Inflorescence:

*Description.*—Umbellate inflorescence occurring in the axis along the underside of branches.

*Number of flowers per inflorescence.*—1-3.

*Number of flowers per plant.*—More than 1000.

*Flowering season.*—April in Mills River, N.C.

*Inflorescence.*—Diameter: Avg. 1.2 cm (0.9 to 1.8 cm). Height: About 1 cm.

*Flower.*—Diameter: About 1 cm. Height: About 0.5 cm.

*Bud.*—Shape: Rounded. Length: About 0.3 cm. Diameter: About 0.3 cm. Color: Red (RHS 46A). Texture: Glabrous.

*Petals.*—Number: 5-6 petals. Arrangement: Whorled. Shape: Ovate. Length: About 0.4 cm. Width: About 0.2 cm. Margin: Entire. Apex: Obtuse. Base: Acute. Color: Yellow (RHS 8B). Texture: Glabrous.

*Sepal.*—Number: 6. Arrangement: Whorled. Shape: Ovate. Length: About 0.5 cm. Width: About 0.3 cm. Margin: Entire. Apex: Obtuse. Base: Acute. Color: Yellow (RHS 8B), often with a stripe of Red (RHS 46A) on the back of the sepal. Texture: Glabrous.

*Peduncle.*—Length: Less than 1 cm. Diameter: Less than 0.1 cm. Color: Varies from Yellow (RHS 8B) to Red (RHS 46C). Texture: Glabrous.

Reproductive organs:

*Gynoecium.*—Pistil number: 1. Pistil length: About 0.2 cm. Stigma shape: Disc-shaped. Stigma color: Yellow-Green (RHS 150B). Style length: Less than 0.2 cm. Style color: Greyed-Yellow (RHS 160C).

*Androecium*.—Stamen number: 5-6. Filament length: About 0.2 cm. Filament color: Yellow (RHS 8B). Anther shape: Bilobed. Anther length: About 0.1 cm. Anther color: Yellow (RHS 8B). Amount of pollen: Average. Pollen color: Yellow (RHS 8B).

Fruit and seed:

*Fruit*.—Type: Drupe. Shape: Ovoid. Length: About 0.8 cm. Width: About 0.5 cm. Color: Red (RHS 46B). Texture: Glabrous.

*Seed*.—Number per fruit: 1 to 2. Shape: Ovoid. Length: About 0.6 cm. Width: About 0.3 cm. Color: Brown (RHS 200B). Texture: Glabrous, shiny.

Disease and insect resistance: 'NCBT3' is documented to be resistant to Wheat Rust (*Puccinia* spp.) as determined by the USDA-ARS Cereal Disease Laboratory, 2017. Neither resistance nor susceptibility to other diseases and pests of *Berberis* have been observed.

Cold hardiness: At least USDA zone 6b; testing has not been completed in colder zones.

What is claimed is:

1. A new and distinct cultivar of *Berberis* plant named 'NCBT3' as illustrated and described herein.

* * * * *